US011740307B2

(12) United States Patent
Sacolick et al.

(10) Patent No.: US 11,740,307 B2
(45) Date of Patent: Aug. 29, 2023

(54) TECHNIQUES FOR DYNAMIC CONTROL OF A MAGNETIC RESONANCE IMAGING SYSTEM

(71) Applicant: Hyperfine Operations, Inc., Guilford, CT (US)

(72) Inventors: Laura Sacolick, Guilford, CT (US); Jonathan Lowthert, Stamford, CT (US); Jeremy Christopher Jordan, Cromwell, CT (US); Hadrien A. Dyvorne, New York, NY (US)

(73) Assignee: Hyperfine Operations, Inc., Guilford, CT (US)

( * ) Notice: Subject to any disclaimer, the term of this patent is extended or adjusted under 35 U.S.C. 154(b) by 430 days.

(21) Appl. No.: 16/830,633

(22) Filed: Mar. 26, 2020

(65) Prior Publication Data
US 2020/0337587 A1 Oct. 29, 2020

Related U.S. Application Data

(60) Provisional application No. 62/839,177, filed on Apr. 26, 2019.

(51) Int. Cl.
*A61B 5/055* (2006.01)
*G01R 33/385* (2006.01)
*G01R 33/44* (2006.01)
*G01R 33/54* (2006.01)

(52) U.S. Cl.
CPC ............ *A61B 5/055* (2013.01); *G01R 33/385* (2013.01); *G01R 33/445* (2013.01); *G01R 33/543* (2013.01); *G01R 33/546* (2013.01)

(58) Field of Classification Search
CPC .... A61B 5/055; G01R 33/385; G01R 33/445; G01R 33/543; G01R 33/546
See application file for complete search history.

(56) References Cited

U.S. PATENT DOCUMENTS

| 5,144,242 | A |   | 9/1992 | Zeilenga et al. |
|---|---|---|---|---|
| 5,349,296 | A |   | 9/1994 | Cikotte et al. |
| 6,160,397 | A | * | 12/2000 | Washburn ........ G01R 33/56554 324/309 |
| 9,541,616 | B2 |   | 1/2017 | Rothberg et al. |
| 9,547,057 | B2 |   | 1/2017 | Rearick et al. |
| 9,625,544 | B2 |   | 4/2017 | Poole et al. |
| 9,645,210 | B2 |   | 5/2017 | McNulty et al. |
| 9,817,093 | B2 |   | 11/2017 | Rothberg et al. |

(Continued)

OTHER PUBLICATIONS

International Search Report and Written Opinion for International Application No. PCT/US2020/024860 dated Jul. 27, 2020.
(Continued)

*Primary Examiner* — G. M. A Hyder
(74) *Attorney, Agent, or Firm* — Foley & Lardner LLP

(57) ABSTRACT

Techniques are described for controlling components of a Magnetic Resonance Imaging (MRI) system with a single controller, such as a Field Programmable Gate Array (FPGA), by dynamically instructing the controller to issue commands to the components using a processor coupled to the controller. According to some aspects, the controller may issue commands to the components of the MRI system whilst actively receiving commands from the processor to be later issued to the components.

20 Claims, 12 Drawing Sheets

(56) References Cited

U.S. PATENT DOCUMENTS

| | | | |
|---|---|---|---|
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,310,037 B2 | 6/2019 | McNulty et al. | |
| 10,416,264 B2 | 9/2019 | Sofka et al. | |
| 10,551,452 B2 | 2/2020 | Rearick et al. | |
| 10,591,561 B2 | 3/2020 | Sacolick et al. | |
| 10,709,387 B2 | 7/2020 | Poole et al. | |
| 2014/0278195 A1* | 9/2014 | Feiweier | G16H 40/63 702/116 |
| 2014/0285196 A1* | 9/2014 | Liu | G01N 24/081 324/309 |
| 2016/0128592 A1 | 5/2016 | Rosen et al. | |
| 2016/0131727 A1 | 5/2016 | Sacolick et al. | |
| 2017/0276749 A1* | 9/2017 | Hugon | G01R 33/383 |
| 2018/0143274 A1* | 5/2018 | Poole | A61B 6/4405 |
| 2018/0143280 A1* | 5/2018 | Dyvorne | G01R 33/389 |
| 2019/0038233 A1 | 2/2019 | Poole et al. | |
| 2019/0324098 A1 | 10/2019 | McNulty et al. | |
| 2019/0353723 A1 | 11/2019 | Dyvome et al. | |
| 2019/0353726 A1 | 11/2019 | Poole et al. | |
| 2020/0022611 A1 | 1/2020 | Nelson et al. | |
| 2020/0022612 A1 | 1/2020 | McNulty et al. | |
| 2020/0034998 A1 | 1/2020 | Schlemper et al. | |
| 2020/0041588 A1 | 2/2020 | O'Halloran et al. | |
| 2020/0045112 A1 | 2/2020 | Sacolick et al. | |
| 2020/0058106 A1 | 2/2020 | Lazarus et al. | |
| 2020/0150202 A1 | 5/2020 | Hugon et al. | |
| 2020/0200844 A1 | 6/2020 | Boskamp et al. | |
| 2020/0209334 A1 | 7/2020 | O'Halloran et al. | |

OTHER PUBLICATIONS

PCT/US2020/024860, Jul. 27, 2020, International Search Report and Written Opinion.

* cited by examiner

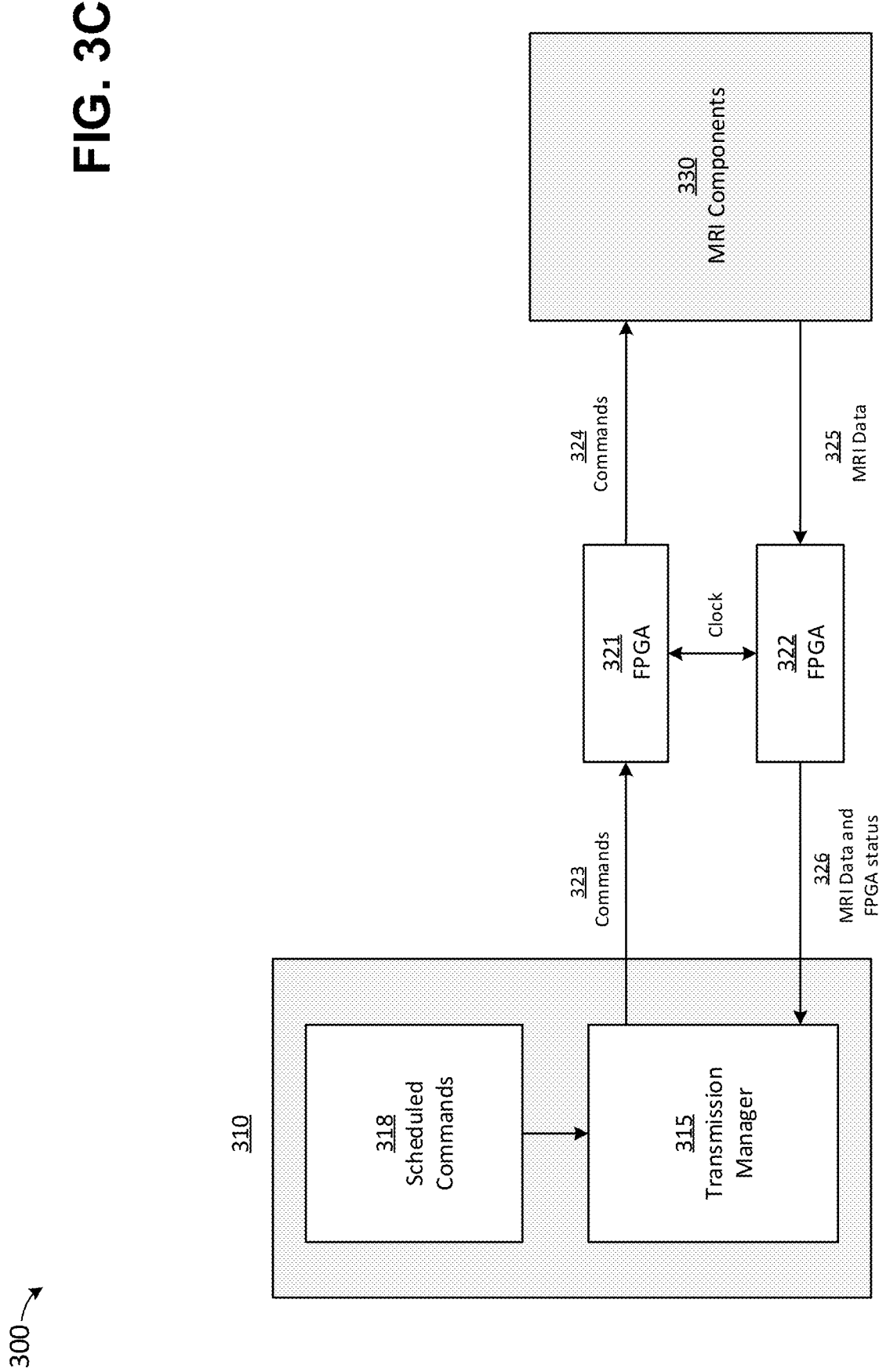

TECHNIQUES FOR DYNAMIC CONTROL OF A MAGNETIC RESONANCE IMAGING SYSTEM

CROSS-REFERENCE TO RELATED APPLICATIONS

This applications claims the benefit of priority under 35 U.S.C. § 119(e) to U.S. Provisional Application Ser. No.: 62/839,177, titled "TECHNIQUES FOR DYNAMIC CONTROL OF A MAGNETIC RESONANCE IMAGING SYSTEM" filed on Apr. 26, 2019, which is incorporated by reference herein in its entirety.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

SUMMARY

According to some aspects, a magnetic resonance imaging (MRI) system is provided, comprising one or more components configured to acquire magnetic resonance data when operated, at least one processor, and a first controller configured to control the one or more components to operate in accordance with a first pulse sequence at least in part by receiving, from the at least one processor, a sequence of commands for controlling the one or more components to operate in accordance with the first pulse sequence, and issuing at least one command of the sequence of commands to the one or more components before completing reception of the sequence of commands from the at least one processor.

According to some aspects, a method of performing magnetic resonance imaging (MRI) within an MRI system comprising one or more components configured to acquire magnetic resonance data when operated is provided, the method comprising receiving, by a first controller from at least one processor, a sequence of commands for controlling the one or more components of the MRI system to operate in accordance with a first pulse sequence, and issuing, by the first controller, at least one command of the sequence of commands to the one or more components of the MRI system before completing reception of the sequence of commands from the at least one processor.

According to some aspects, at least one non-transitory computer readable storage medium storing instructions that, when executed by circuitry part of an MRI system comprising one or more components configured to acquire magnetic resonance data when operated, cause the MRI system to perform a method of performing magnetic resonance imaging, the method comprising receiving, by a first controller from at least one processor, a sequence of commands for controlling the one or more components of the MRI system to operate in accordance with a first pulse sequence, and issuing, by the first controller, at least one command of the sequence of commands to the one or more components of the MRI system before completing reception of the sequence of commands from the at least one processor.

In some embodiments, the first controller is a Field Programmable Gate Array (FPGA). In some embodiments, the first controller and the at least one processor are connected via a Universal Serial Bus (USB) connection and the first controller receives commands of the sequence of commands via the USB connection.

In some embodiments, the MRI system further comprises a second controller coupled to the first controller and configured to receive data from the one or more components. In some embodiments, the second controller is configured to provide said data received from the one or more components to the at least one processor. In some embodiments, the second controller is further configured to provide an indication of available memory in the first controller to the at least one processor. In some embodiments, the first controller and second controller are synchronized via a common clock signal.

In some embodiments, the one or more components comprises an RF coil, a first gradient coil and a second gradient coil, and wherein the sequence of commands includes commands to operate at least the RF coil, the first gradient coil and the second gradient coil to produce the first pulse sequence. In some embodiments, the one or more components includes at least one RF coil and at least one gradient coil.

In some embodiments, the one or more components comprise at least one permanent $B_0$ magnet configured to produce a $B_0$ field. In some embodiments, the one or more components comprise an amplifier and one or more magnetics components, and wherein the sequence of commands includes commands to operate the one or more magnetics components through operation of the amplifier. In some embodiments, the at least one permanent $B_0$ magnet is configured to produce a $B_0$ field of less than or equal to approximately 0.1 T and greater than or equal to approximately 50 mT. In some embodiments, the at least one permanent $B_0$ magnet comprises a plurality of concentric permanent magnet rings.

In some embodiments, the MRI system further comprises a power system configured to operate the MRI system using an average of less than 10 kilowatt during acquisition of said magnetic resonance data.

In some embodiments, the sequence of commands is a first sequence of commands, and wherein the first controller is further configured to: receive, from the at least one processor, a second sequence of commands for controlling the one or more components to operate in accordance with a second pulse sequence; and issue at least one command of the second sequence of commands to the one or more components before completing reception of the second sequence of commands from the at least one processor.

In some embodiments, the method of performing magnetic resonance imaging (MRI) within an MRI system further comprises receiving data from the one or more components by a second controller coupled to the first controller. In some embodiments, the method further comprises providing said data received from the one or more components from the second controller to the at least one processor. In some embodiments, the method further comprises providing an indication of available memory of the first controller from the second controller to the at least one processor.

In some embodiments, the sequence of commands is a first sequence of commands, and the method further comprises: receiving, by the first controller from the at least one processor, a second sequence of commands for controlling the one or more components of the MRI system to operate in accordance with a second pulse sequence; and issuing, by the first controller, at least one command of the second sequence of commands to the one or more components of the MRI system before completing reception of the second sequence of commands from the at least one processor.

According to some aspects, at least one non-transitory computer readable storage medium is provided storing processor-executable instructions that, when executed by at least one processor, cause the at least one processor to perform accessing a control waveform for controlling one or more components of a magnetic resonance imaging (MRI) system, compressing the control waveform to obtain a compressed control waveform, and transmitting the compressed control waveform to a Field Programmable Gate Array (FPGA) configured to operate the one or more components of the MRI system.

According to some aspects, a method for controlling one or more magnetics components of a magnetic resonance imaging (MRI) system is provided, the method comprising accessing a control waveform for controlling the one or more magnetic components of the MRI system, compressing the control waveform to obtain a compressed control waveform, and transmitting the compressed control waveform to a Field Programmable Gate Array (FPGA) configured to operate the one or more magnetic components of the MRI system.

According to some aspects, a magnetic resonance imaging (MRI) system is provided. The MRI system comprises one or more magnetics components and at least one processor configured to perform: accessing a control waveform for controlling the one or more magnetic components of the MRI system, compressing the control waveform to obtain a compressed control waveform, and transmitting the compressed control waveform to a Field Programmable Gate Array (FPGA) configured to operate the one or more magnetic components of the MRI system.

In some embodiments, compressing the control waveform comprises: determining a desired waveform density as a function of time; and calculating a plurality of time index and waveform amplitude pairs based at least in part on the desired waveform density, the plurality of time index and waveform amplitude pairs representing the compressed control waveform. In some embodiments, the time indexes of the plurality of time index and waveform amplitude pairs are irregularly sampled in time.

In some embodiments, the one or more magnetic components include a gradient coil, and wherein the control waveform is a waveform for controlling the gradient coil.

In some embodiments, compressing the control waveform further comprises calculating a cumulative probability distribution function of the control waveform and interpolating the calculated cumulative probability distribution function based on the desired waveform density. In some embodiments, determining the desired waveform density comprises calculating a probability density function of the control waveform. In some embodiments, calculating the probability density function of the control waveform comprises calculating first and second derivatives of the control waveform with respect to time. In some embodiments, calculating the probability density function of the control waveform is based at least in part on one or more constants that control a density of the compressed control waveform.

In some embodiments, transmitting the compressed control waveform to the FPGA comprises transmitting the compressed control waveform to the FPGA via a Universal Serial Bus (USB) connection.

In some embodiments, the compressed control waveform is transmitted to the FPGA via a plurality of commands.

In some embodiments, the MRI system comprises at least one permanent magnet configured to produce a $B_0$ field of less than or equal to approximately 0.1 T and greater than or equal to approximately 50 mT.

In some embodiments, the method for controlling one or more magnetics components of the MRI system further comprises using the compressed control waveform to issue commands to operate the one or more magnetic components of the MRI system.

The foregoing apparatus and method embodiments may be implemented with any suitable combination of aspects, features, and acts described above or in further detail below. These and other aspects, embodiments, and features of the present teachings can be more fully understood from the following description in conjunction with the accompanying drawings.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIGS. 3A-3C each depicts an MRI system in which commands are generated and issued to operate MRI components, according to some embodiments;

DETAILED DESCRIPTION

Figure 1:
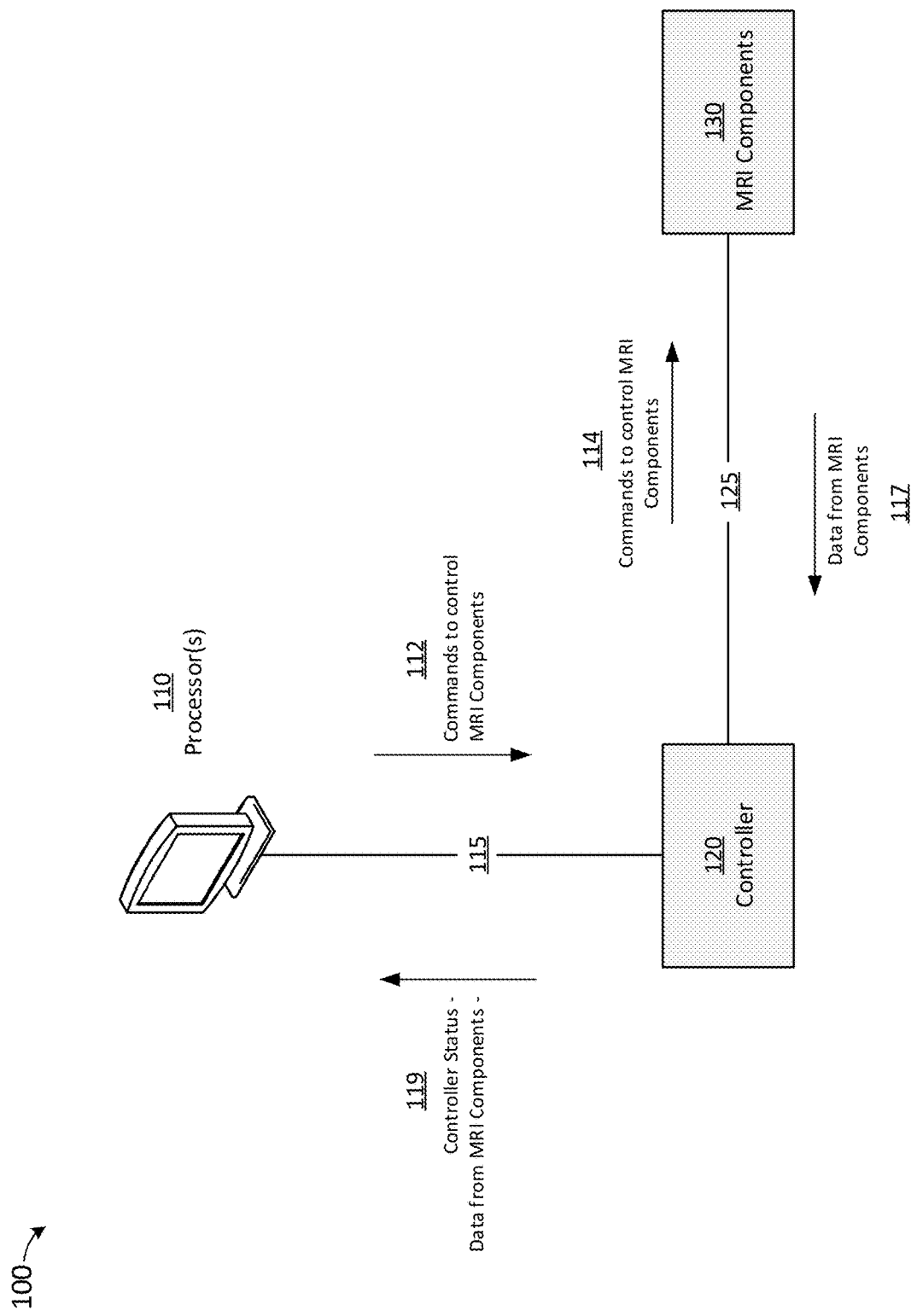
FIG. 1 depicts an illustrative MRI system, according to some embodiments.

An MRI system typically includes various MRI components, which may include a $B_0$ magnet, magnetic shims, RF coils which transmit and receive MR signals, gradient coils which vary the $B_0$ field, and various power components. To operate the MRI components to produce images, these components are controlled to operate in concert with one another with precise timing. For instance, events like initiating of image acquisition, setting the frequency or phase of a signal transmitted by an RF coil, transmitting an RF pulse with an RF coil, etc. are typically controlled so that they occur with a precision on the order of nanoseconds.

To meet these stringent timing requirements, magnetics components are conventionally controlled using a bank of Field Programmable Gate Arrays (FPGAs) or other programmable controllers, which are each preloaded with a sequence of commands. During operation of the MRI system, each controller executes the preloaded sequence of commands, and together these commands control the components of the MRI system. Each of the controllers can execute a single command at a time but are preloaded so that, when the controllers are synchronized with a common clock signal, commands are issued from the controllers to the components of the MRI system at intended times.

Generally in conventional systems, a controller is selected for each of the different controllable components of the MRI system so that each controller independently issues commands to one "channel" of the system. For instance, one controller may issue commands to a particular RF coil, whereas another controller may issue commands to a particular gradient coil. This configuration allows the system to preload all of the commands onto the controller and, during operation, to issue all of the commands at exactly the desired times. This configuration requires a large bank of controllers to function, however, as well as a step of preloading all the commands onto the controller prior to operation.

The inventors have developed techniques enabling control of components of an MRI system with a single controller, such as an FPGA, by dynamically instructing the controller to issue commands to the components using a processor coupled to the controller. In this configuration, the controller may issue commands to the components of the MRI system whilst also actively receiving commands from the processor to be later issued to the components. In contrast to conventional MRI systems, the single controller may not issue all of the commands at exactly the desired times, and the single controller may not be preloaded with all of the commands.

Due to the stringent timing requirements of an MRI system discussed above, a single controller issuing commands to components of the MRI system may conventionally be unable to transmit all commands at their desired times because some of the commands may overlap in time and because the controller is unable to transmit multiple commands at the same time. Moreover, the volume of commands necessary to control the components of the MRI system may be sufficiently large that a single controller may simply not have sufficient bandwidth to send all of the commands, even if the timing constraints were to be relaxed to some extent. Furthermore, unlike the above-described conventional approach in which a number of controllers are preloaded with separate sequences of commands, the memory of a single controller may be insufficient to store a sequence of commands necessary for performing an entire pulse sequence prior to performance of the pulse sequence.

The inventors have developed techniques that address these issues and thereby enable control of components of an MRI system with a single controller. These techniques include a process of scheduling a controller to issue commands to components of an MRI system with relaxed timing requirements that are informed by a command prioritization system. The techniques further include a process for compressing waveforms to be sent to components of the MRI system, which thereby reduce the number of commands necessary to be sent by the controller to control the components.

According to some embodiments, a controller may be configured to receive commands from one or more processors and issue those commands to one or more components of an MRI system whilst receiving further commands from the one or more processors. These commands may, when issued to the one or more components of the MRI system, control the one or more components to operate in accordance with a pulse sequence. In some cases, the controller may receive commands from one or more processors and issue those commands to one or more components of an MRU system whilst providing MRI data received from the one or more components of the MRI system to the one or more processors. Operation of the MRI system may comprise the one or more processors sending and receiving data to and from the controller whilst the controller is sending and receiving data to and from components of the MRI system.

According to some embodiments, the controller of an MRI system may be configured to only issue commands to one or more components of an MRI system and a second controller may be configured to receive data from the one or more components. In this arrangement, a single controller may still control components of an MRI system, but that controller's available bandwidth may be increased by not relying on the single controller to also receive data from the components. In some cases the controller configured to transmit to the components may also receive the commands from one or more processors whilst the other controller may transmit data to the one or more processors.

The MRI scanner market is overwhelmingly dominated by high-field systems, and particularly for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

Following below are more detailed descriptions of various concepts related to, and embodiments of, techniques for controlling magnetics components of an MRI system with a single controller. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 depicts an illustrative MRI system, according to some embodiments. System 100 includes one or more processors 110, a controller 120 and components of the MRI system 130. The components 130 may, for instance, include various power management and magnetics components used to perform imaging using the MRI system 100.

In the example of FIG. 1, the controller 120 is configured to receive commands 112 from the processor(s) 110 via communication link 115 and issue commands 114 to the components of the MRI system 130 via communication link 125. The communication link 115 may include, for example, a Universal Serial Bus (USB) connection. Commands 112 received by the controller 120 from the processor(s) 110 may be, in at least some cases, stored in a memory buffer of the controller prior to issuing the command to one or more of the MRI components 130. Data 117 produced by the MRI components (e.g., imaging data) is transmitted to controller 120 via communication link 125. Data 119 may comprise the data 117 produced by the MRI components and may be transmitted to the processor(s) 110 by the controller 120 via communication link 115. In addition, data 119 may comprise status information (e.g., memory usage) relating to the controller 120.

It will be appreciated that commands 112 and commands 114 may not be identical to one another, as the manner in which the processor(s) 110 instructs the controller 120 to issue commands to the MRI components may not generally be the same as the manner in which the controller 120 controls said components. For instance, commands 112 may include a command to control an RF coil and to control the RF coil in a particular way at a particular time. The controller 120 may, in response to receiving this command, control the voltage of the RF coil (and/or power components associated with the RF coil). Accordingly, issuing commands to the MRI components 130 may, as referred to herein, comprise or may consist of controlling the voltage, phase, frequency and/or other characteristics of one or more of the components.

Similarly, data 117 provided from the MRI components 130 to the controller 120 may be communicated to the processor(s) 110 through data 119 in any suitable manner, and is not limited to retransmitting the received data by the controller. For example, the controller 120 may reformat or otherwise edit the received data 117 to produce the data 119.

According to some embodiments, controller 120 may buffer commands received from the processor(s) 110 and issue those commands to the MRI components 130 at a time specified by the command (or by data associated with the command provided by the processor(s) 110). Concurrently, commands may be transmitted from the processor(s) 110 to the controller 120 and stored by the controller, and data may be transmitted from the controller 120 to the processor(s) 110. As such, data transfer via communication link 115 may be managed separately from data transfer via communication link 125. In particular, decisions as to when data is transferred to and from the controller via communication link 115 may be controlled by the processor(s) 110 as discussed below. In contrast, data is transferred from the controller to one or more of the MRI components 130 via communication link 125 according to the timing of commands being issued, and data (e.g. imaging data) is received from MRI components by the controller via communication link 125 as it is produced by the MRI components.

According to some embodiments, controller 120 may be a single FPGA. The clock frequency of the FPGA may, in some embodiments, be at least 50 MHz so that the timing requirements of issuing commands to one or more of the MRI components may be met. One illustrative FPGA model that may be employed as controller 120 is the Intel 5AGXMB3G4F35C4N, which has a core clock speed of 100 MHz.

In some embodiments, controller 120 may be implemented as a pair of FPGAs in which communication from the processor(s), to the controller and to the MRI components is directed through one of the FPGAs, whilst communication from the MRI components, to the controller and to the processor(s) is directed through the other FPGA.

According to some embodiments, processor(s) 110 may execute a transmission manager configured to manage data transfer via communication link 115 by determining when to transmit commands to the controller 120. The controller 120 may subsequently transmit the commands received from the processor(s) 110 to one or more of the MRI components 130 at a time indicated by the command (and/or by data associated with the command). In addition, the transmission manager may be configured to determine when to receive data from the controller 120 (which may include data from one or more of the MRI components such as imaging data, and data indicative of the status of the controller).

In some embodiments, the transmission manager executed by the processor(s) 110 may determine when to transmit commands to the controller 120 and when to receive data from the controller 120 prior to initiating imaging via the MRI components 130. That is, a schedule describing when transmission and reception are performed by the processor(s) 110, and what each transmission and reception event constitutes, may be determined in advance of imaging. As one example, if a dense sequence of commands are scheduled to be transmitted by the controller to the MRI components and there is a subsequent break in transmission of commands to the MRI components, the processor(s) 110 may schedule transmission of commands to the controller and/or reception of data from the controller during that break period.

Alternatively, data transfer and reception by the processor(s) 110 may be, to at least some extent, dynamically adapted during imaging. In some embodiments, the transmission manager executed by processor(s) 110 may monitor memory usage of the controller 120 and determine whether to transmit commands to the controller and/or to receive data from the controller based on the memory usage. An indication of memory usage of the controller 120 may, for instance, be transmitted to the processor(s) periodically by the controller, in response to a request from the processor(s), and/or whenever imaging data is provided to the processor(s) from the controller. Since transmitting data from the processor(s) 110 to the controller 120 may decrease the memory available to the controller, and receiving data obtained from MRI components 130 from the controller by the processor(s) 110 may increase the controller's available memory, the processor(s) may determine whether to transmit or receive based on current memory usage of the controller and the extent to which the controller is storing commands not yet issued to the MRI components. For instance, the processor(s) may schedule data transfer to ensure that the controller does not run out of available memory, and that the controller always has commands buffered to be issued to the MRI components.

According to some embodiments, processor(s) 110 may execute a scheduler configured to determine timings of the various commands to be issued by the controller 120 to the MRI components 130. As discussed above, a single controller issuing commands to components of the MRI system may be unable to transmit all commands at desired times because some of the commands may overlap in time and because the controller is unable to transmit multiple commands at the same time. By prioritizing certain commands over others, processor(s) 110 may determine suitable timings at which the commands are to be issued by the controller 120 to the MRI components such that the MRI system may be operated as intended and commands can be issued serially to the MRI components.

According to some embodiments, the scheduler executed by the processor(s) may identify priority levels associated with different types of commands and may determine, based on the priority levels, which commands may be issued at a different time than desired without negatively impacting operation of the MRI system. For instance, commands that must be issued with very precise timing may be treated with a highest priority level by the scheduler and may be scheduled to be issued to the MRI system at, or very close to, a desired time. Commands with a lower requirement for precision timing may be treated with any of a number of lower priority levels, allowing the scheduler to vary times at which these commands are to be issued to the MRI system if necessary to avoid temporal overlap of commands.

In some embodiments, processor(s) 110 may be configured to compress waveform data when generating commands to transmit to the controller 120. As discussed above, compressing waveforms to be sent to components of the MRI system may reduce the number of commands necessary to be sent by the controller to control the components. As used herein, a waveform refers to time-varying signal that, when provided to a component of the MRI system, operates the component in a particular manner. For example, to produce a pulse sequence from a magnetic coil of the MRI system, a waveform may be transmitted to the coil and/or to components associated with the coil such as an amplifier, to drive the coil to produce the desired pulse sequence. Commands issued by the controller 120 to MRI components 130 may indicate the amplitude of one or more points along a waveform such that the waveform may be expressed as a sequence of commands.

As used herein, a pulse sequence may, in some cases, refer to a sequence of commands to be executed by each of multiple components of an MR system including, for example, one or more RF coils of the MR system and one or more gradient coils of the MR system. In some embodiments, the commands may indicate the types of pulses to be generated by the RF and/or gradient coil(s). The sequence of commands may be in any suitable format, as aspects of the technology described herein are not limited in this respect. The sequence of commands may be specified at different levels of granularity; for instance, one command provided from processor(s) 110 to controller 120 may specify multiple voltages of a pulse sequence, whereas the controller 120 may issue individual voltages of that sequence as multiple separate commands to the MRI components 130.

Figure 2:
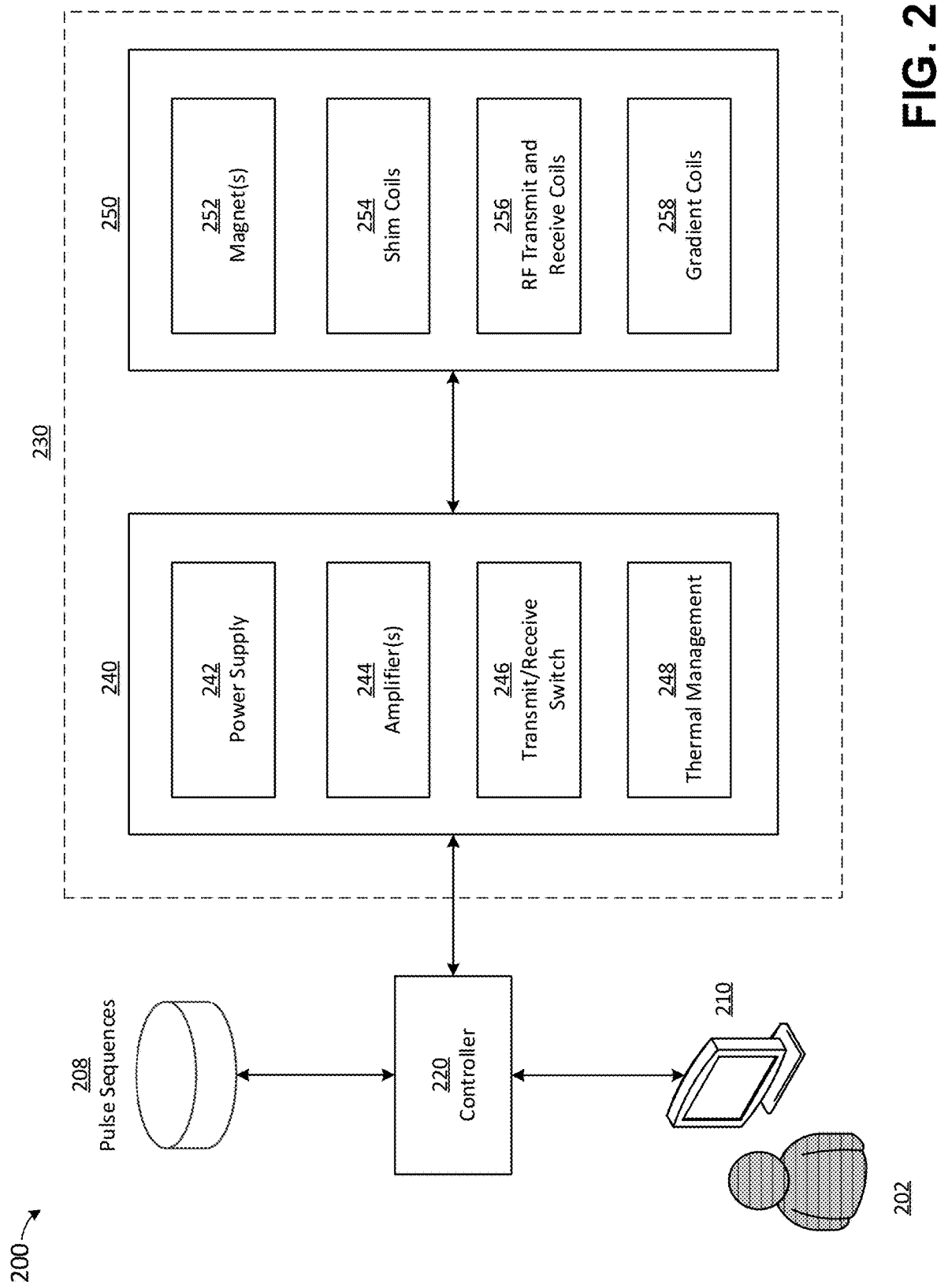
FIG. 2 depicts components of an illustrative MRI system, according to some embodiments.

FIG. 2 depicts components of an illustrative MRI system, according to some embodiments. MRI system 200 is depicted to provide one illustrative example of a set of MRI components 230 that may be operated to generate imaging data. In the example of FIG. 2, MRI components 230 includes power management components 240 and magnetics components 250. MRI system 200 may be an example of MRI system 100 shown in FIG. 1, for example, with the processor(s) 110, controller 120 and MRI components 130 being represented in the example of FIG. 2 by computing device 210, controller 220 and MRI components 230, respectively.

As illustrated in FIG. 2, MRI system 200 includes controller 220, which is configured to issue commands to the power management components 240 of the MRI components 250. Controller 220 may be configured to implement one or more pulse sequences, which are used to determine commands that may be sent to power management system 240 to operate the magnetic components 250 in a desired sequence (e.g., parameters for operating the RF transmit and receive coils 256, parameters for operating gradient coils 258, etc.). As illustrated in FIG. 2, controller 220 is configured to communicate with computing device 210, which is programmed to process received MR data. For example, computing device 210 may process received MR data to generate one or more MR images using any suitable image reconstruction process(es). Controller 220 may provide information produced from one or more pulse sequences to computing device 210 for the processing of data by the computing device. For example, controller 220 may provide information about one or more pulse sequences to computing device 210 and the computing device may perform an image reconstruction process based, at least in part, on the provided information.

In the example of FIG. 2, magnetics components 250 comprise magnet(s) 252, shim coils 254, RF transmit and receive coils 256, and gradient coils 258. Magnet(s) 252 may be used to generate the main magnetic field $B_0$ of the MRI system 200. Magnet(s) 252 may be any suitable type or combination of magnetics components that can generate a desired main magnetic $B_0$ field. In some implementations, the $B_0$ magnet may be formed using superconducting material generally provided in a solenoid geometry and may utilize cryogenic cooling systems to keep the $B_0$ magnet in a superconducting state. In some cases, magnet(s) 252 may comprise a $B_0$ magnet that is a low-field $B_0$ magnet (e.g., a $B_0$ magnet operating at 0.2 T). In some cases, the $B_0$ magnet may be a permanent magnet.

Figure 9:
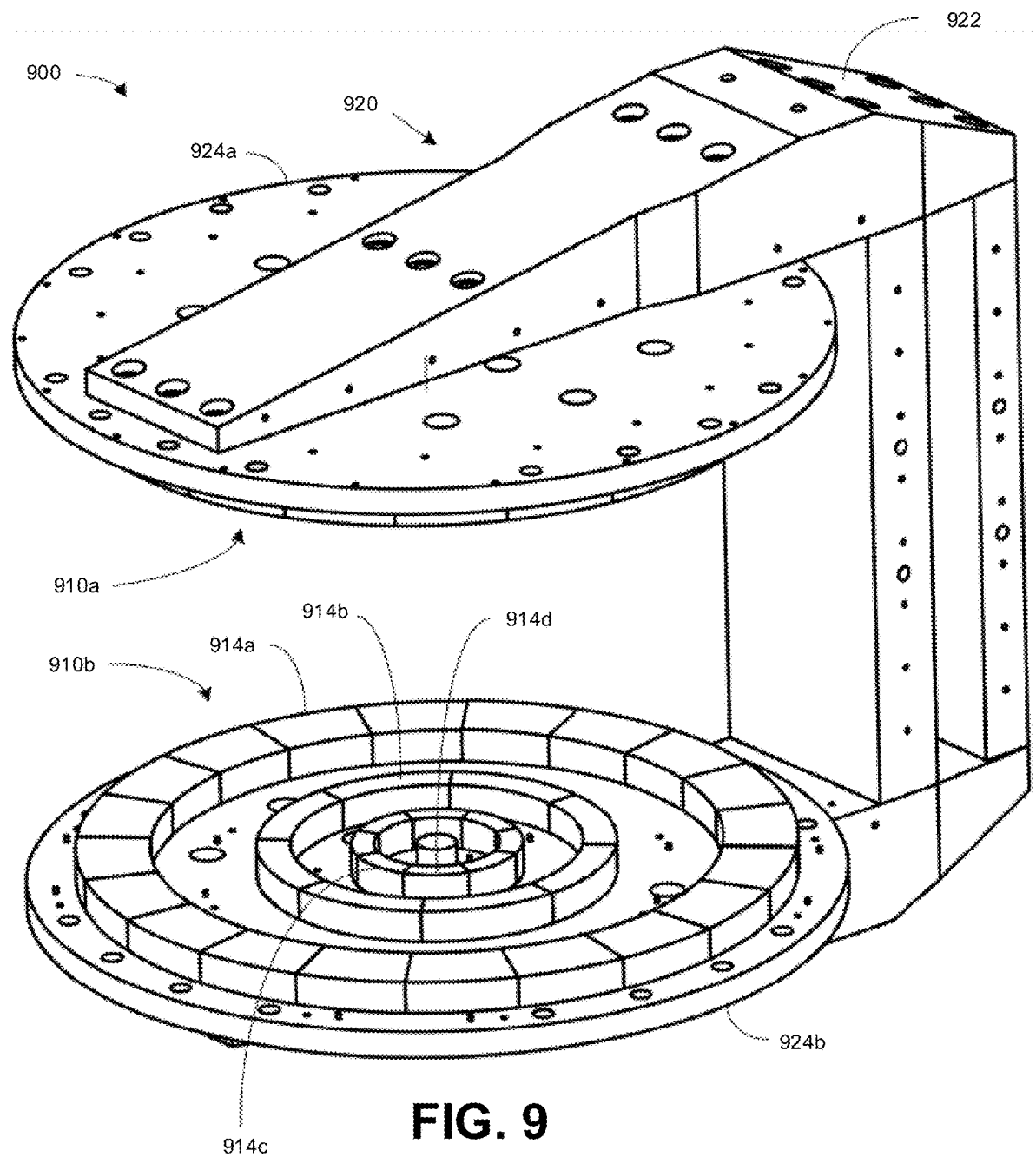
FIG. 9 illustrates a $B_0$ magnet comprising a plurality of permanent magnets, according to some embodiments.

One illustrative example of a $B_0$ magnet that is a permanent magnet is shown in FIG. 9. FIG. 9 illustrates a $B_0$ magnet 900, in accordance with some embodiments. In particular, $B_0$ magnet 900 is formed by permanent magnets 910a and 910b arranged in a bi-planar geometry with a ferromagnetic yoke 920 coupled thereto to capture electromagnetic flux produced by the permanent magnets and transfer the flux to the opposing permanent magnet to increase the flux density between permanent magnets 910a and 910b. Each of permanent magnets 910a and 910b are formed from a plurality of concentric permanent magnet rings, as shown by permanent magnet 910b comprising an outer ring of permanent magnets 914a, a middle ring of permanent magnets 914b, an inner ring of permanent magnets 914c, and a permanent magnet disk 914d at the center. Permanent magnet 910a may comprise the same set of permanent magnet elements as permanent magnet 910b. The permanent magnet material used may be selected depending on the design requirements of the system (e.g., NdFeB, SmCo, etc. depending on the properties desired).

The permanent magnet rings are sized and arranged to produce a homogenous field of a desired strength in the central region (field of view) between permanent magnets 910a and 910b. In particular, in the exemplary embodiment illustrated in FIG. 9, each permanent magnet ring comprises a plurality of circular arc segments sized and positioned to produce a desired $B_0$ magnetic field, as discussed in further detail below. Yoke 920 is configured and arranged to capture magnetic flux generated by permanent magnets 910a and 910b and direct it to the opposing side of the $B_0$ magnet to increase the flux density in between permanent magnets 910a and 910b. Yoke 920 thereby increases the field strength within the field of view of the $B_0$ magnet with less permanent magnet material, reducing the size, weight and cost of the $B_0$ magnet. Yoke 920 also comprises a frame 922 and plates 924a and 924b that, in a manner similar to that described above in connection with yoke 920, captures and circulates magnetic flux generated by the permanent magnets 910a and via the magnetic return path of the yoke to increase the flux density in the field of view of the $B_0$ magnet. The structure of yoke 920 may be similar to that described above to provide sufficient material to accommodate the magnetic flux generated by the permanent magnets and providing sufficient stability, while minimizing the amount of material used to, for example, reduce the cost and weight of the $B_0$ magnet. In some embodiments, the $B_0$ magnet 900 may be configured to generate a static B0 field having a field strength between 0.05 Tesla and 0.1 Tesla. Additional examples of B0 magnets and/or yokes that may be used in some embodiments are described in U.S. Pat. No. 10,281,541, titled "Low-Field Magnetic Resonance Imaging Methods and Apparatus," dated May 7, 2019, which is incorporated by reference herein in its entirety Returning to FIG. 2, according to some embodiments gradient coils 258 may be arranged to provide gradient fields and, for example, may be arranged to generate gradients in the $B_0$ field in three substantially orthogonal directions (X, Y, Z). Gradient coils 258 may be configured to encode emitted MR signals by systematically varying the $B_0$ field (the $B_0$ field generated by magnet(s) 252 and/or shim coils 254) to encode the spatial location of received MR signals as a function of frequency or phase. For example, gradient coils 258 may be configured to vary frequency or phase as a linear function of spatial location along a particular direction, although more complex spatial encoding profiles may also be provided by using nonlinear gradient coils. For example, a first gradient coil may be configured to selectively vary the $B_0$ field in a first (X) direction to perform frequency encoding in that direction, a second gradient coil may be configured to selectively vary the $B_0$ field in a second (Y) direction substantially orthogonal to the first direction to perform phase encoding, and a third gradient coil may be configured to selectively vary the $B_0$ field in a third (Z) direction substantially orthogonal to the first and second directions to enable slice selection for volumetric imaging applications.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 2, RF transmit and receive coils 256 comprise one or more transmit coils that may be used to generate RF pulses to induce an oscillating magnetic field $B_1$. The transmit coil(s) may be configured to generate any suitable types of RF pulses.

In the example of FIG. 2, power management system 240 includes electronics to provide operating power to one or more components of the MRI system 200. For example, power management system 240 may include one or more power supplies, gradient power components, transmit coil components, and/or any other suitable power electronics needed to provide suitable operating power to energize and operate components of MRI system 200. As illustrated in FIG. 2, power management system 240 comprises power supply 242, power component(s) 244, transmit/receive switch 246, and thermal management components 248 (e.g., cryogenic cooling equipment for superconducting magnets). Power supply 242 includes electronics to provide operating power to magnetic components 250 of the MRI system 200. For example, power supply 242 may include electronics to provide operating power to one or more $B_0$ coils (e.g., $B_0$ magnet 252) to produce the main magnetic field for the low-field MRI system. Transmit/receive switch 246 may be used to select whether RF transmit coils or RF receive coils are being operated.

Power component(s) 244 may include one or more RF receive (Rx) pre-amplifiers that amplify MR signals detected by one or more RF receive coils (e.g., coils 256), one or more RF transmit (Tx) power components configured to provide power to one or more RF transmit coils (e.g., coils 256), one or more gradient power components configured to provide power to one or more gradient coils (e.g., gradient coils 258), and one or more shim power components configured to provide power to one or more shim coils (e.g., shim coils 254).

As illustrated in FIG. 2, MRI system 200 includes controller 220 (which may also be referred to as a console) having control electronics to send instructions to and receive information from power management system 240. Controller 220 may be configured to implement one or more pulse sequences, which are used to determine the instructions sent to power management system 240 to operate the magnetic components 250 in a desired sequence (e.g., parameters for operating the RF transmit and receive coils 256, parameters for operating gradient coils 258, etc.). As illustrated in FIG. 2, controller 220 also interacts with computing device 210 programmed to process received MR data. For example, computing device 210 may process received MR data to generate one or more MR images using any suitable image reconstruction process(es). Controller 220 may provide information about one or more pulse sequences to computing device 210 for the processing of data by the computing device. For example, controller 220 may provide information about one or more pulse sequences to computing device 210 and the computing device may perform an image reconstruction process based, at least in part, on the provided information. In conventional MRI systems, computing device 210 typically includes one or more high performance work-stations configured to perform computationally expensive processing on MR data relatively rapidly.

Figure 3A:
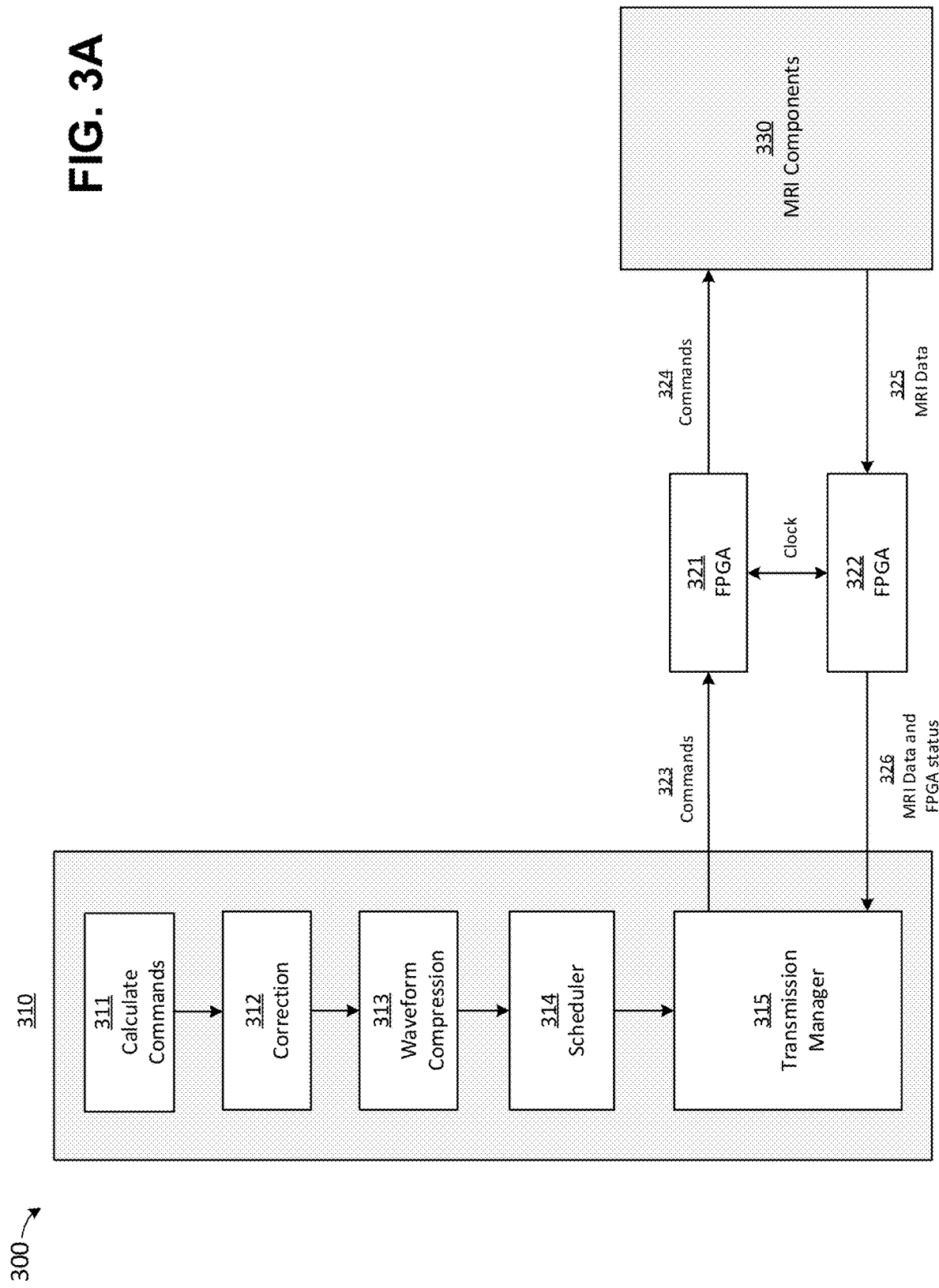

FIG. 3A depicts an MRI system in which commands are generated and issued to operate MRI components, according to some embodiments. MRI system 300 includes one or more processors 310 configured to perform a number of processing steps 311-315 to be discussed below, which generate commands to be transmitted to the FPGA 321 and determine when to perform said transmission during operation of the MRI system. The FPGA 321 is configured to issue commands 323 to one or more of the MRI components 330. MRI data 325 produced from MRI components 330 is transmitted to the FPGA 322, which is operated in a synchronous mode with the FPGA 321 via a common clock signal. The FPGA 322 is configured to transmit at least some of the MRI data 325 received (and/or data derived from the MRI data 325) to the processor(s) 310, and furthermore may transmit data relating to the status of the FPGA 322 to the processor(s) 310, such as an indication of the available memory of the FPGA 322. MRI components 330 may comprise, for instance, any of the components shown as MRI component 230 in FIG. 2 and/or other components not shown in FIG. 2.

In the example of FIG. 3A, processor(s) 310 are configured to execute processing units 311-315 via hardware, software or a combination of both, and may be executed via any number of suitable processors, including one or more general purpose CPUs and/or microprocessors.

In the example of FIG. 3A, processing unit 311 calculates an idealize sequence of commands that, if sent to MRI components 330, would operate the components to perform a desired sequence of imaging. The idealized command sequence may comprise sub-sequences for generating desired pulse sequences by MRI components and may be calculated via conventional techniques for controlling MRI components.

In the example of FIG. 3A, correction unit 312 calculates corrections to the sequence of commands calculated in act 311. These corrections may adjust for various physical characteristics of the MRI components and/or the process of transmitting commands to the MRI components that the idealized commands calculated in act 311 do not account for. As not-limiting example, correction unit 312 may correct the commands for known physical delays in transmitting commands from the FPGA to one or more MRI components of the components 330, for known delays in operation of the FPGA and/or the process of sending commands to the FPGA (e.g., via a USB link) and/or may apply system calibration parameters to the commands.

According to some embodiments, waveform compression unit 313 may perform waveform compression to reduce an amount of data represented by the corrected sequence of commands produced by correction unit 312. As discussed above, sequences of commands that represent an ordered set of amplitudes to be issued to one or more MRI components may be termed a waveform. In waveform compression unit 313, new waveforms may be generated through a process of compression of the idealized, corrected commands representing an initial waveform. An example of this process is discussed in further detail below.

According to some embodiments, scheduler 314 may perform scheduling of the calculated sequence of commands (which may include compressed waveforms generated in waveform compression unit 313). As discussed above, a single FPGA may generally not be able to issue the intended sequence of commands to the MRI components because some of the commands may temporally overlap and a single FPGA cannot transmit multiple different commands at the same time. Scheduling operations performed by processing unit 314 may adjust the relative timing of at least some of the commands in the sequence of commands so that the single FPGA 321 is able to control the MRI components 330 whilst meeting the timing requirements necessary for proper MRI imaging. An example of this process is discussed in further detail below.

According to some embodiments, transmission manager 315 may determine when to transmit commands to the FPGA 321 for subsequent transmission to MRI components 330, and when to receive data from the FPGA 322. Operation of a transmission manager is discussed above in relation to controller 120 in FIG. 1, and transmission manager 315 may be configured in any of the various ways described above. In particular, in some embodiments the transmission manager 315 may determine when to transmit commands to the FPGA 321 and when to receive data from the FPGA 322 prior to initiating imaging via the MRI components 330. In some embodiments, the transmission manager 315 may monitor memory usage of FPGA 321 and FPGA 322, and determine whether to transmit commands to the FPGA 321 and/or to receive data from FPGA 322 based on their respective memory usage. For example, transmission manager 315 may schedule data reception to ensure that FPGA 322 does not run out of available memory whilst also ensuring that FPGA 321 always has commands buffered to be issued to the MRI components 330.

Figure 3B:
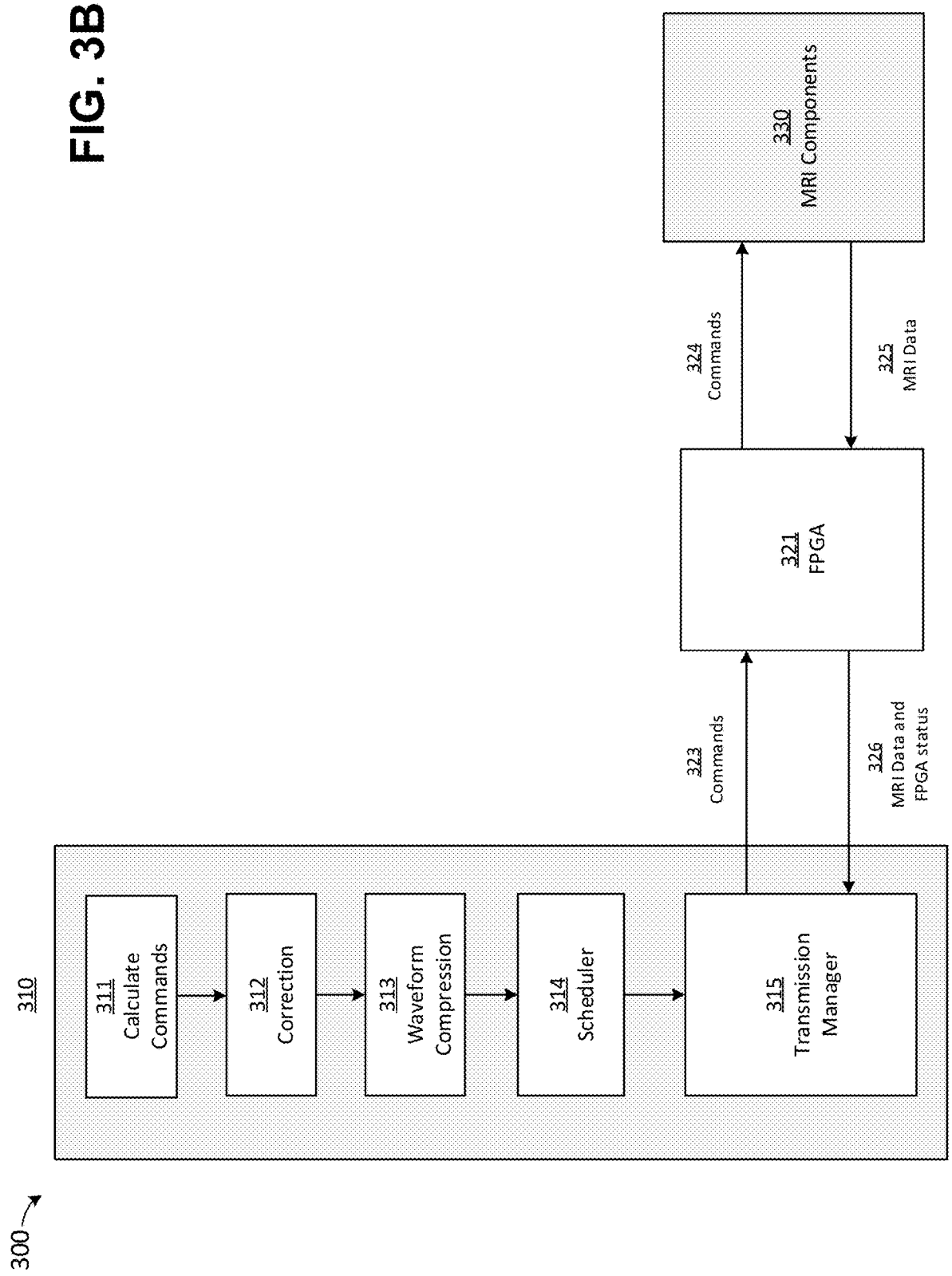

FIGS. 3B and 3C depict variations of system 300, according to some embodiments. In the example of FIG. 3B, FPGA 321 is configured to perform both issuance of commands 324 to the MRI components 330 and reception of MRI data 325 from the MRI components. In addition, FPGA 321 both receives commands 323 from the transmission manager 315 and transmits data 326 comprising MRI data and status information relating to the FPGA 321 to the transmission manager.

In the example of FIG. 3C, processor(s) 310 is configured to access previously scheduled commands 318 and manager transmission of said commands 323 using the transmission manager.

Figure 4A:
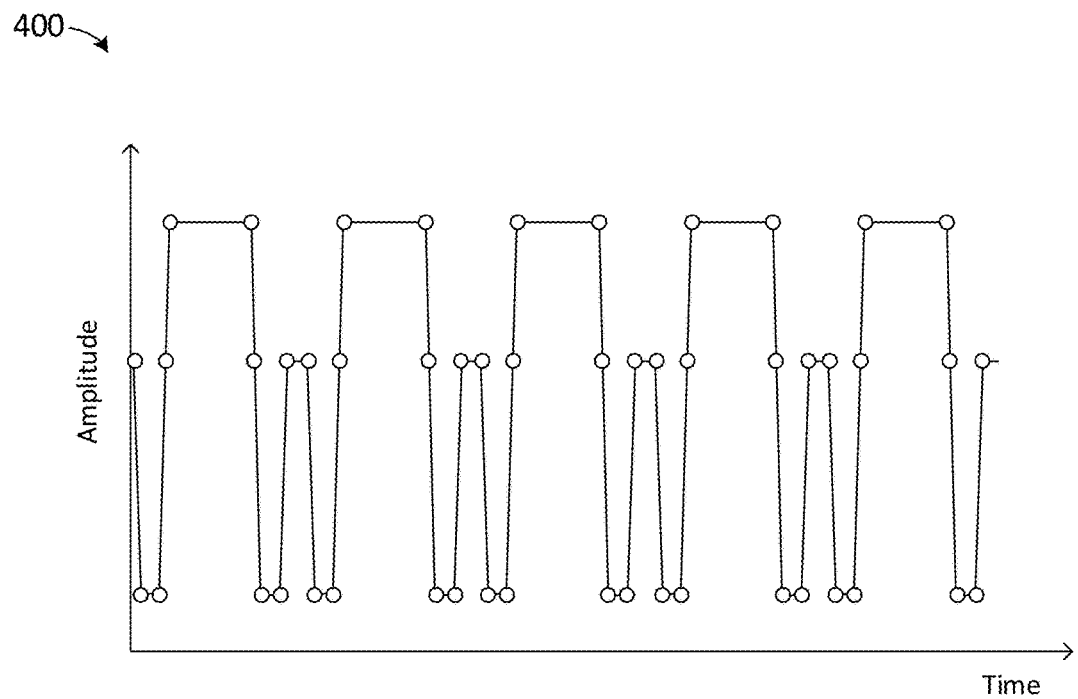
FIG. 4A illustrates an example of an idealized gradient field waveform that may be produced by one or more magnetics components of an MRI system, according to some embodiments.

FIG. 4A illustrates an example of an idealized gradient field waveform that may be produced by one or more magnetics components of an MRI system, according to some embodiments. To provide one illustrative example of waveform compression, waveform 400 represents an ideal gradient field waveform to be created by one or more components of an MRI system (e.g., by one or more gradient coils). In the example of FIG. 4A, the circles represent ideal instructions to be sent to the MRI components, whereas the line connecting the circles represents the analog output of the component resulting from the instructions. For example, a gradient coil may be instructed to produce a signal with the amplitudes given by the time-amplitude waveform 400 via the sequence of time index and waveform amplitude pairs represented by the circles in FIG. 4A, which may cause the coil to produce an amplitude over time as shown by the solid line.

For multiple reasons, however, simply issuing such a sequence to a gradient coil (e.g., via an associated amplifier) would not cause the coil to produce the illustrated waveform. Rather, a waveform that corrects for a number of physical issues such as eddy currents, hysteresis, amplifier imperfections and gradient anisotropy must be generated that, when applied, will produced the desired gradient waveform.

Figure 4B:
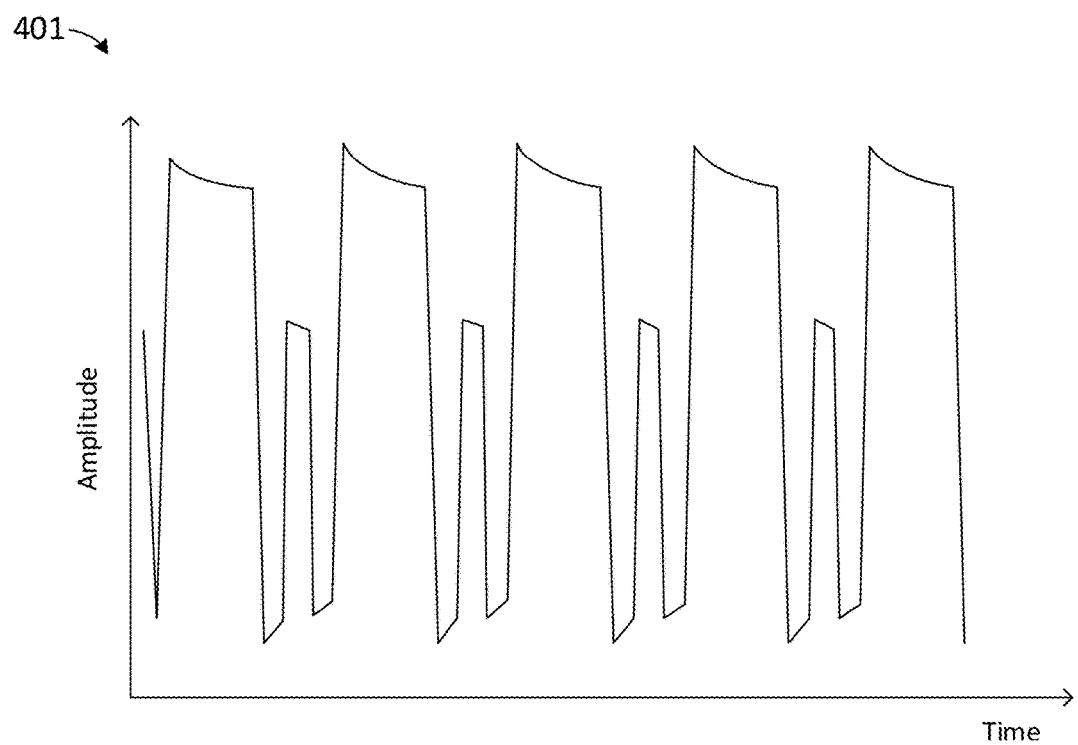
FIG. 4B illustrates an example of a waveform that may be provided to one or more components of an MRI system so that the gradient field waveform of FIG. 4A may be produced by one or more magnetics components, according to some embodiments.

FIG. 4B illustrates an example of such a waveform, wherein waveform 401 represents a waveform that, when issued to gradient coil (or amplifier associated with a gradient coil), is intended to cause the coil to produce the waveform 400 shown in FIG. 4A. In this example, waveform 401 is more complex than waveform 400 in that more data points would be necessary to describe this waveform than were necessary for waveform 400.

As discussed above, there may be a need to reduce data issued to MRI components in the above-described MRI systems 100, 200 or 300 shown in FIG. 1, 2 or 3, respectively, by a respective command to the MRI component(s), as a result of using a single controller to issue commands to the MRI component(s). According to some embodiments, a waveform such as waveform 401 may be compressed to reduce the amount of data points necessary to describe it, and thereby reduce the number (and/or size) of commands necessary to control an MRI component in the intended manner.

Figure 4C:
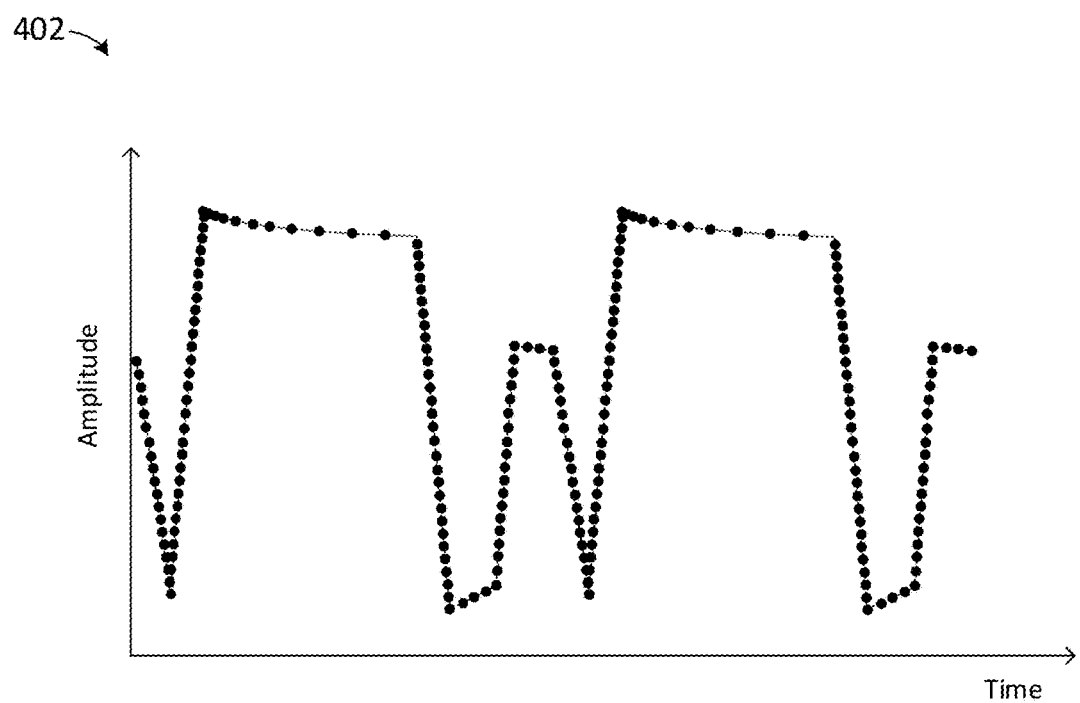
FIG. 4C illustrates a compressed waveform corresponding to the waveform of FIG. 4B, according to some embodiments.

As one example, FIG. 4C illustrates a compressed waveform corresponding to the waveform of FIG. 4B, according to some embodiments. In the example of FIG. 4C, waveform 402 is described by a number of data points (shown as solid circles) that together approximate the waveform of FIG. 4B (shown in FIG. 4C as a solid line, albeit with a different scaling along the time axis).

Various compression techniques may be applied to compress a waveform, and the example of FIG. 4C in which the data points are not regularly spaced along the time axis represents one illustrative approach that will be described further below.

Figure 5:
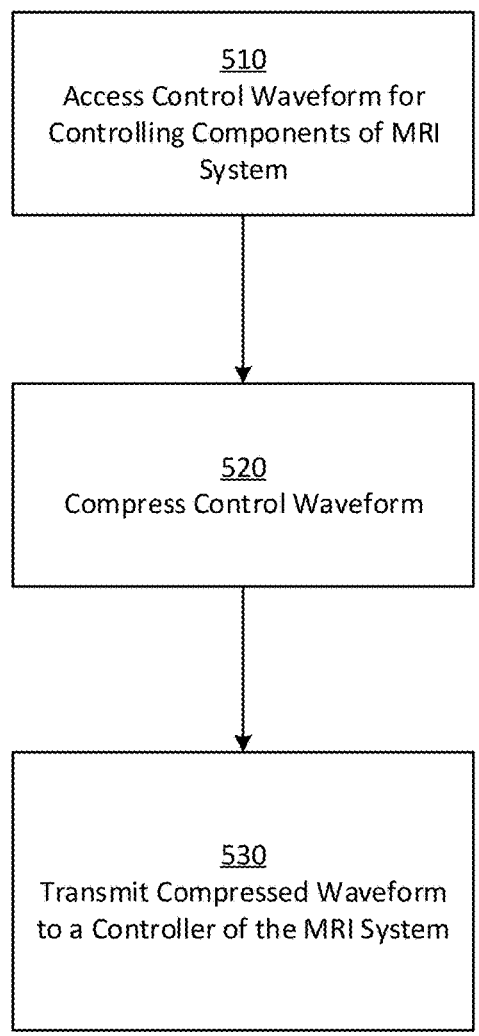
FIG. 5 is a flowchart of a method of generating compressed waveforms for control of components of an MRI system, according to some embodiments.

FIG. 5 is a flowchart of a method of generating compressed waveforms for control of components of an MRI system, according to some embodiments. Method 500 begins with act 501 in which a control waveform for controlling one or more components of an MRI system is accessed. Said access may comprise reading waveform data from one or more computer readable storage media and/or receiving waveform data via a communication link. Waveform 401 shown in FIG. 4B is an illustrative example of a suitable control waveform that, when applied to one or more components of an MRI system, will control the component(s) to perform a desired sequence of actions (e.g., generate a pulse sequence).

In act 520, the control waveform accessed in act 510 is compressed via any suitable technique. According to some embodiments, the control waveform, which may be represented as G(t), may be compressed via the following steps.

First, calculate first and second derivatives of G(t) with respect to time—G'(t) and G''(t). Second, compute a probability density function (PDF) for the waveform as:

$$PDF(t) = (|G'(t)| + C_1|G''(t)|)^{C_2}$$

where $C_1$ and $C_2$ are constants used to control the density of the compressed waveform and thereby the final number of commands produced.

Third, compute a cumulative distribution function (CDF) as:

$$CDF(t) = \Sigma PDF(t)$$

Fourth, compute the inverse CDF and choose compressed waveform indices by interpolating the CDF to a desired output compressed waveform resolution. This produces a set of reduced time indices $t_c$ where $t_c$ may not be regularly sampled in time. The compressed waveform is thereby given as $G(t_c)$.

According to some embodiments, the above algorithm may be modified by calculating an error term that allows the calculation of additional indices if the error caused by the compression is above some threshold value. For example, the error term windowed over a suitable time window $t_1$ to $t_2$ may be:

$$err(t) = \int_{t_1}^{t_2} G(t) - \int_{t_1}^{t_2} G(t_c)$$

Based on this error term, additional indices may be calculated if the error metric is considered too large.

In some embodiments, certain waveform time points may be defined as particularly important and kept in the final sequence of time index and amplitude pairs, even if the compression algorithm would otherwise not include such a time-amplitude pair.

In act 530, the resulting compressed waveform, which may for instance be represented as a set of time index and amplitude pairs as discussed in the above technique, is transmitted to a controller of the MRI system for subsequent issuance to one or MRI components. The compressed waveform may be transmitted via any number of commands, including via a single command for each time-amplitude data point of the waveform.

Figure 6:
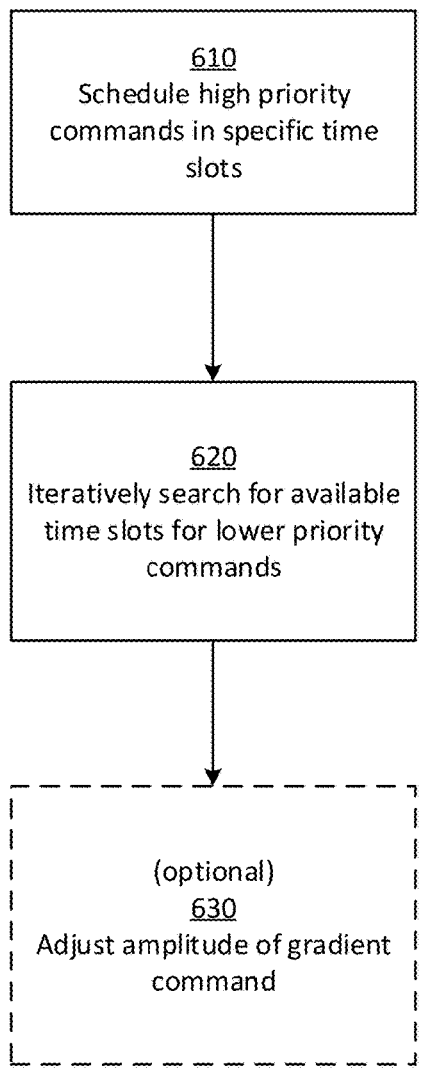
FIG. 6 is a flowchart of a method of scheduling commands to be transmitted to components of an MRI system by a controller, according to some embodiments.

FIG. 6 is a flowchart of a method of scheduling commands to be transmitted to components of an MRI system by a controller, according to some embodiments. Method 600 may be performed by, for instance, the scheduler 314 shown in FIGS. 3A and 3B, or processor(s) 210 or 110 shown in FIGS. 2 and 1, respectively.

In the example of FIG. 6, irrespective of the device performing method 600, the method is configured to act upon a sequence of commands and, to the extent that any of the commands are scheduled to be issued to components of an MRI system at overlapping times, to adjust the relative timing of the commands to avoid any overlaps whilst meeting timing requirements for the MRI system. Method 600 may rely upon information that indicates a prioritization level for each type of command as discussed below. A type of command may be referred to below as a "channel," although it will be appreciated that there may be only a single physical transmission connection between a controller and MRI components and that "channel" refers to a conceptual division and not necessary a physical one.

Method 600 begins in act 610 in which commands in high priority channels are fixed at their intended times. Act 610 may in some cases merely comprise accessing data that indicates that certain commands are not to be moved in time during scheduling, and may not comprise any active action of "fixing" the commands in time.

In act 620, the device performing method 600 performs an iterative search for available time slots for any lower priority commands (that is, lower priority than the high priority commands fixed in act 610). Any number of additional priority levels may be considered and timing requirements associated with each.

As one example, an MRI system may consider RF commands such as RF transmit, signal receive, RF phase, RF frequency and RF clock reset to be high priority and thereby fixed in time. Commands such as gradient commands may be assigned a middle priority level and allowed to shift up to 200 ns in time. Other command types, such as data loading instructions, may be assigned a low priority and allowed to shift up to several μs in time.

As an optional step in act 630, any gradient commands that were adjusted in time in act 620 may be modified to compensate for the different time at which the command is going to be issued. In particular, the amplitude of a gradient command may be adjusted based on the time shift applied in act 620.

Figure 7:
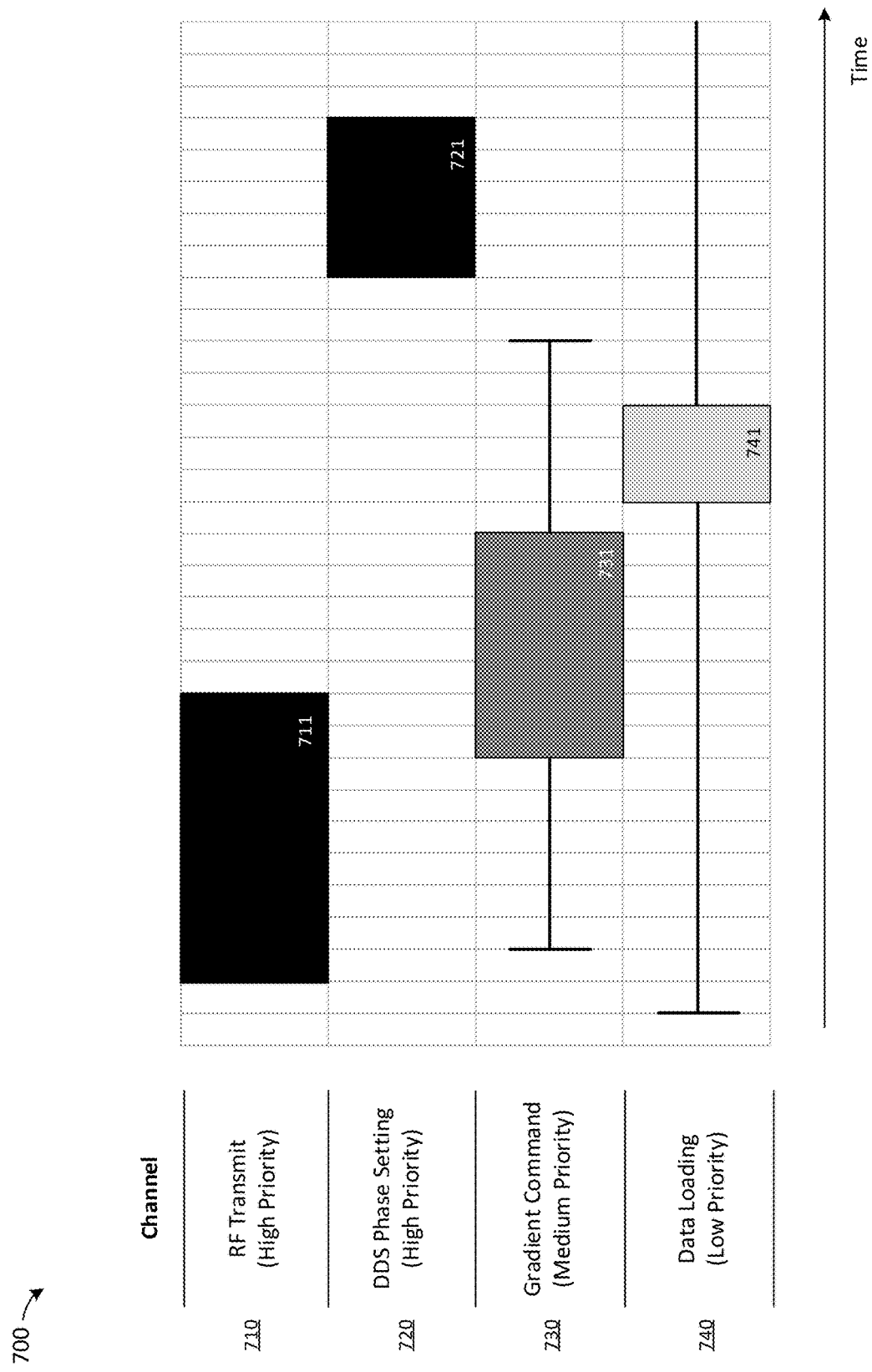
FIG. 7 depicts an example of scheduling commands to be transmitted to components of an MRI system by a controller according to command priority, according to some embodiments.

FIG. 7 depicts one example of scheduling commands to be transmitted to components of an MRI system by a controller according to command priority, according to some embodiments. Chart 700 illustrates a visual example of applying the scheduling process of method 600. In particular, four channels 710, 720, 730 and 740 are considered as a simple example and have associated priority levels as shown. The grid in FIG. 7 represents time units of a size that corresponds to the inverse of the frequency of the controller issuing the commands to the MRI components. That is, each block has a width corresponding to one clock cycle of the controller.

As can be seen in FIG. 7, the commands 711 and 731 are overlapping in time and need to be scheduled appropriately for each of the illustrated commands to be issued by a single controller. The horizontal bars on opposing sides of each command represent timing requirements associated with the channel and/or with the priority level of the channel.

According to some embodiments, a scheduling algorithm operating upon the four commands of FIG. 7 may recognize that the command 711 is high priority and cannot be moved and, as such, the command 731 must be moved to not overlap with this command. In moving command 731, however, it will inevitably then overlap with command 741. Since channel 741 is of a lower priority than channel 730, the scheduler may for instance move command 731 to the next time at which it is no longer overlapping with the higher priority command 711 (i.e., two clock cycles later in FIG. 7). The command 741 can then be moved to a later time at which it is not temporally overlapping with other commands.

Figure 8:
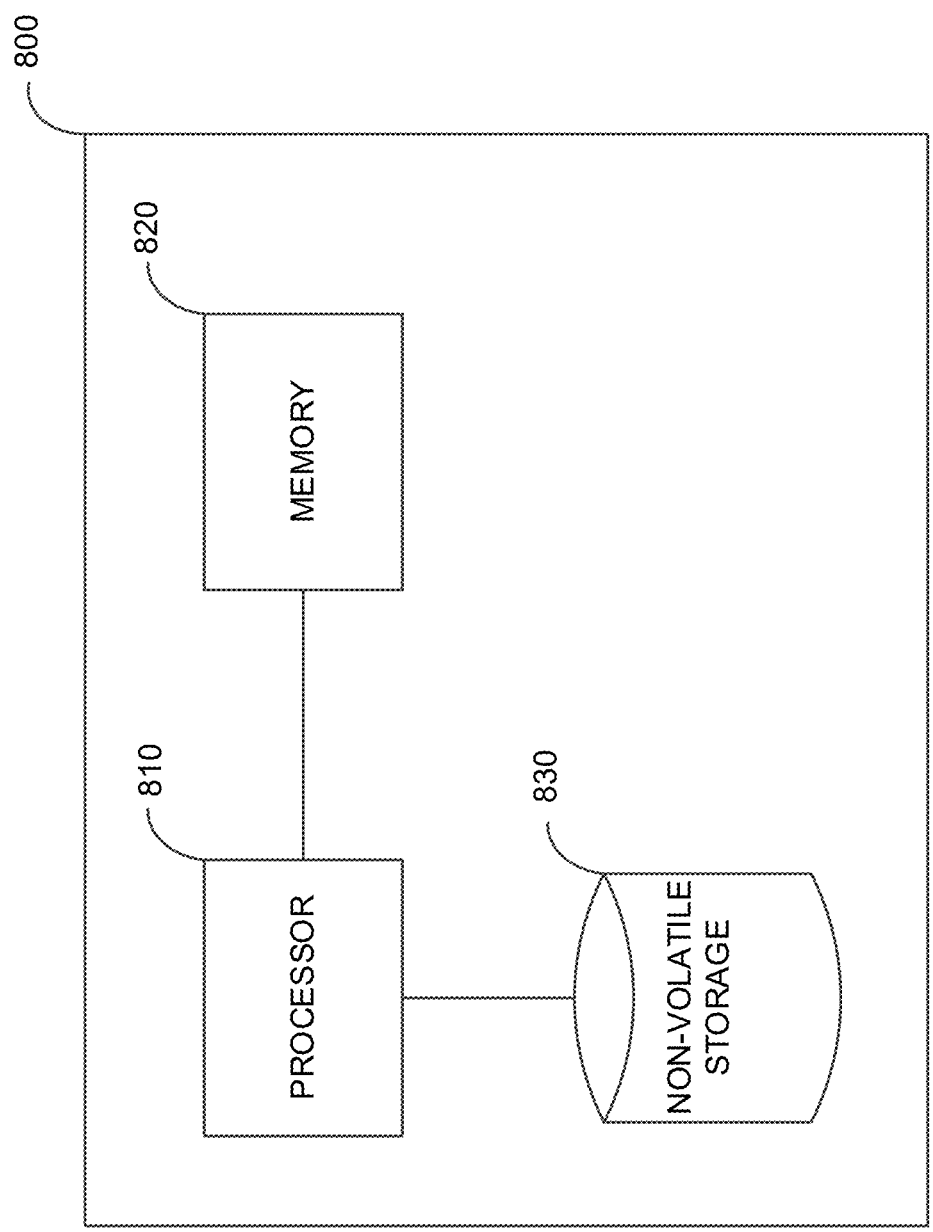
FIG. 8 illustrates an example of a computing system environment on which aspects of the present application may be implemented.

An illustrative implementation of a computer system 800 that may be used to perform any of the aspects of dynamic control of a magnetic resonance imaging system is shown in FIG. 8. The computer system 800 may include one or more processors 810 and one or more non-transitory computer-readable storage media (e.g., memory 820 and one or more non-volatile storage media 830). The processor 810 may control writing data to and reading data from the memory 820 and the non-volatile storage device 830 in any suitable manner, as the aspects of the technology described herein are not limited in this respect. To perform functionality and/or techniques described herein, the processor 810 may execute one or more instructions stored in one or more computer-readable storage media (e.g., the memory 820, storage media, etc.), which may serve as non-transitory computer-readable storage media storing instructions for execution by the processor 810.

In connection with techniques described herein, code used to, for example, compress a waveform, analyze MRI imaging data, manage transmission/reception of data to/from a controller, execute a scheduler, etc. may be stored on one or more computer-readable storage media of computer system 800. Processor 810 may execute any such code to provide any techniques for dynamic control of a magnetic resonance imaging system as described herein. Any other software, programs or instructions described herein may also be stored and executed by computer system 800. It will be appreciated that computer code may be applied to any aspects of methods and techniques described herein. For example, computer code may be applied to interact with an operating system to transmit or receive data through conventional operating system processes, such as conventional USB operating system processes.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the technology described herein. The non-transitory computer-readable medium or media may be transportable, such that the program or programs stored thereon may be loaded onto any computer resource to implement various aspects of the technology described herein as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the technology described herein need not reside on a single computer or processor, but may be distributed in a modular fashion among different computers or processors to implement various aspects of technology described herein.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The terms "approximately," "substantially" and "about" may be used to mean within ±20% of a target value in some embodiments, within ±10% of a target value in some embodiments, within ±5% of a target value in some embodiments, and yet within ±2% of a target value in some embodiments. The terms "approximately," "substantially" and "about" may include the target value.

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments in detail, various modifications and improvements will readily occur to those skilled in the art. Such modifications and improvements are intended to be within the spirit and scope of the disclosure. Accordingly, the foregoing description is by way of example only, and is not intended as limiting.

What is claimed is:

1. A magnetic resonance imaging (MRI) system, comprising:
    one or more components configured to acquire magnetic resonance data when operated;
    at least one controller comprising a first controller; and
    at least one processor configured to determine times to issue individual commands from the first controller to the one or more components,
    wherein the first controller is configured to control the one or more components to operate in accordance with a first pulse sequence at least in part by:
        receiving, from the at least one processor, a sequence of commands for controlling the one or more components to operate in accordance with the first pulse sequence; and
        issuing at least one command of the sequence of commands to the one or more components, in accordance with the determined times to issue the at least one command, before completing reception of the sequence of commands from the at least one processor.

2. The MRI system of claim 1, wherein the first controller is a Field Programmable Gate Array (FPGA).

3. The MRI system of claim 1, wherein the first controller and the at least one processor are connected via a Universal Serial Bus (USB) connection and the first controller receives commands of the sequence of commands via the USB connection.

4. The MRI system of claim 1, further comprising a second controller coupled to the first controller and configured to receive data from the one or more components.

5. The MRI system of claim 4, wherein the second controller is configured to provide said data received from the one or more components to the at least one processor.

6. The MRI system of claim 5, wherein the second controller is further configured to provide an indication of available memory in the first controller to the at least one processor.

7. The MRI system of claim 4, wherein the first controller and second controller are synchronized via a common clock signal.

8. The MRI system of claim 1, wherein the one or more components comprises an RF coil, a first gradient coil and a second gradient coil, and wherein the sequence of commands includes commands to operate at least the RF coil, the first gradient coil and the second gradient coil to produce the first pulse sequence.

9. The MRI system of claim 1, wherein the one or more components comprise at least one permanent $B_0$ magnet configured to produce a $B_0$ field, wherein the at least one permanent $B_0$ magnet is configured to produce a $B_0$ field of less than or equal to approximately 0.1 T and greater than or equal to approximately 50 mT.

10. The MRI system of claim 1, wherein the one or more components comprise an amplifier and one or more magnetics components, and wherein the sequence of commands includes commands to operate the one or more magnetics components through operation of the amplifier.

11. The MRI system of claim 1, further comprising a power system configured to operate the MRI system using an average of less than 10 kilowatt during acquisition of said magnetic resonance data.

12. The MRI system of claim 1, wherein the sequence of commands is a first sequence of commands, and wherein the first controller is further configured to:
    receive, from the at least one processor, a second sequence of commands for controlling the one or more components to operate in accordance with a second pulse sequence; and
    issue at least one command of the second sequence of commands to the one or more components before completing reception of the second sequence of commands from the at least one processor.

13. The MRI system of claim 1, wherein the determined times are determined at least in part by prioritizing the individual commands.

14. A method of performing magnetic resonance imaging (MRI) within an MRI system comprising one or more components configured to acquire magnetic resonance data when operated, the method comprising:
    receiving, by a first controller from at least one processor configured to determine times to issue individual commands from the first controller to the one or more components, a sequence of commands for controlling the one or more components of the MRI system to operate in accordance with a first pulse sequence; and
    issuing, by the first controller, at least one command of the sequence of commands to the one or more components of the MRI system in accordance with the determined times to issue the at least one command, before completing reception of the sequence of commands from the at least one processor.

15. The method of claim 14, wherein the first controller is a Field Programmable Gate Array (FPGA), the first controller and the at least one processor are connected via a Universal Serial Bus (USB) connection, and the first controller receives commands of the sequence of commands via the USB connection.

16. The method of claim 15, further comprising:
    receiving data from the one or more components by a second controller coupled to the first controller;
    providing the data received from the one or more components from the second controller to the at least one processor.

17. The method of claim 14, wherein the one or more components comprises an RF coil, a first gradient coil and a second gradient coil, and wherein the sequence of commands includes commands to operate at least the RF coil, the first gradient coil and the second gradient coil to produce the first pulse sequence.

18. The method of claim 14, wherein the one or more components comprise an amplifier and one or more magnetics components, and wherein the sequence of commands includes commands to operate the one or more magnetics components through operation of the amplifier.

19. The method of claim 14, wherein the sequence of commands is a first sequence of commands, and wherein the method further comprises:
    receiving, by the first controller from the at least one processor, a second sequence of commands for controlling the one or more components of the MRI system to operate in accordance with a second pulse sequence; and
    issuing, by the first controller, at least one command of the second sequence of commands to the one or more components of the MRI system before completing reception of the second sequence of commands from the at least one processor.

20. At least one non-transitory computer readable storage medium storing instructions that, when executed by circuitry part of an MRI system comprising one or more components configured to acquire magnetic resonance data when operated, cause the MRI system to perform a method of performing magnetic resonance imaging, the method comprising:
    receiving, by a first controller from at least one processor configured to determine times to issue individual commands from the first controller to the one or more components, a sequence of commands for controlling the one or more components of the MRI system to operate in accordance with a first pulse sequence; and
    issuing, by the first controller, at least one command of the sequence of commands to the one or more components of the MRI system in accordance with the determined times to issue the at least one command, before completing reception of the sequence of commands from the at least one processor.

* * * * *